United States Patent
Cotarca et al.

[11] Patent Number: 5,917,067
[45] Date of Patent: *Jun. 29, 1999

[54] PROCESS FOR PRODUCING AN OMEGA-FUNCTIONALIZED ALIPHATIC CARBOXYLIC ACID AND INTERMEDIATE PRODUCTS OF SAID PROCESS, INCLUDING 2-OXEPANONE-7-SUBSTITUTED PRODUCTS

[75] Inventors: Livius Cotarca, Cervignano Del Friuli; Paolo Maggioni, Montevecchia; Alfonso Nardelli, Cervignano Del Fruili; Stefano Sguassero, San Giorgio Di Nogaro, all of Italy

[73] Assignee: Industrie Chimiche Caffaro S.P.A., Milan, Italy

[*] Notice: This patent is subject to a terminal disclaimer.

[21] Appl. No.: 08/556,982

[22] PCT Filed: Jun. 8, 1994

[86] PCT No.: PCT/EP94/01864

§ 371 Date: Apr. 18, 1996

§ 102(e) Date: Apr. 18, 1996

[87] PCT Pub. No.: WO94/29258

PCT Pub. Date: Dec. 22, 1994

[30] Foreign Application Priority Data

Jun. 15, 1993 [IT] Italy .............................. MI93A001271

[51] Int. Cl.$^6$ .................................. C07C 51/16
[52] U.S. Cl. .............................. 554/132; 554/61; 554/62; 554/63; 554/125; 554/141; 554/160; 554/213; 554/219; 554/225; 549/266; 549/272
[58] Field of Search .................................. 554/132, 141, 554/125, 160, 213, 219, 225, 61, 62, 63; 549/266, 272

[56] References Cited

U.S. PATENT DOCUMENTS 4,322,547 3/1982 Minisci et al. .

FOREIGN PATENT DOCUMENTS 7112123 3/1971 Japan .
1203752 9/1967 United Kingdom .

OTHER PUBLICATIONS

CRC Handbook of Chemistry and Physics, 62th ed., 1982.
Chem. abstr., registry number and structure of nonanedioic acid.
Abstract No. 48452 z, Eta–(Beta–Cyanoethyl)Caprolactone, Chemical Abstracts, 75(7):311, 1971.
Murahashi, et al, Fe2O3–Catalyzed Baeyer–Villiger Oxidation of Ketones with Molecular Oxygen in the Presence of Aldehydes, Tetrahedron Letters, 33(49):7557, 1992.
Burns, et al., Highly Reactive Magnesium and its Application to Organic Synthesis, J. of Organic Chemistry, 52(16):3674, 1987.
Zakharkin, et al., Abstract No. 21911 g: 2E–Dodecendioic) Acid from Dodecandioic Acid, Chemical Abstracts, 99(3):569, 1983.
Chem. abstr. 114:224827, 1990.
Chem. abstr. 114:42036, 1990.
Chem. abstr. 112:54951, 1989.
Chem. abstr. 106:84014, 1986.
Chem. abstr. 99:126627, 1983.
Chem. abstr. 96:199098, 1981.
Chem. abstr. 91:74212, 1979.
Chem. abstr. 73:130592, 1970.
Chem. abstr. 53:10044h, 1953.

*Primary Examiner*—Gary Geist
*Assistant Examiner*—Deborah D. Carr
*Attorney, Agent, or Firm*—Henry D. Coleman; R. Neil Sudol

[57] ABSTRACT

A process for producing an omega-functionalized aliphatic carboxylic acid starting from cyclohexanone and omega-functionalized α-olefins or acrylic esters. The process comprises an addition step, an oxidation step, an isomerization step, and one or more hydrogenation steps. The process allows to use raw materials that are available at low cost and to achieve high selectivity and high yield with industrially simple steps. The process includes the production of new intermediate products, including 2-oxepanone-7-substituted products.

48 Claims, No Drawings

PROCESS FOR PRODUCING AN OMEGA-FUNCTIONALIZED ALIPHATIC CARBOXYLIC ACID AND INTERMEDIATE PRODUCTS OF SAID PROCESS, INCLUDING 2-OXEPANONE-7-SUBSTITUTED PRODUCTS

This application is a 371 of PC/1794/01864 filed Jun. 18, 1994.

The present invention relates to a process for producing an omega-functionalized aliphatic carboxylic acid that has over 7 carbon atoms and to the intermediate products of this process, including 2-oxepanone-7-substituted products.

More particularly, the present invention relates to the production of aliphatic carboxylic acids that have more than 7 carbon atoms and can be used in the production of polyamides with a large number of carbon atoms, even more particularly polyamides with 9 carbon atoms (nylon 9 and nylon 6,9). These polyamides are particularly appreciated due to their mechanical and elastic characteristics. Despite this, current worldwide industrial production of polyamide 9 is practically nonexistent due to lack of an industrially feasible process for producing 9 amino nonanoic acid with the required degree of purity.

The present invention furthermore relates particularly to the production of 1,9-nonandioic acid (azelaic acid), which is used in the field of lubricants, polyester and alkyd resins, as plasticizer and as a drug for dermatological use, and in the production of polyamide 6,9.

A process for oxidizing ketones, including cyclic ketones, by using permonosulfuric acid as an oxidizing agent has been known since the last century as the Baeyer-Villiger reaction (A. Von Baeyer and V. Villiger, Ber. 1899, 32, 3265; 1400, 33, 858). Other oxidizing agents have been used for this reaction, such as for example: peracetic acid, described by R. Criegel (Liebig Annalen, 1948, 560, 127) and in UK patent No. 1,203,752, peracid salts such as magnesium permonophthalate described in Syntesis 1015–1017, 1987, or persalts such as sodium perborate, described in U.S. Pat. No. 4,988,825, whereas the agent used most is m-chloroperbenzoic acid. More recently, methods have been described for synthesizing lactones from ketones, using molecular oxygen in the presence of catalysts, Tetrahedron. Lett. 33, 7557–60, 1992. In general, the synthesis of lactones starting from cyclic ketones has unpredictable regioselectivity and chemoselectivity.

Processes for producing polyamides 9 are known and are described by K. A. Pollart and R. E. Miller, (J. Am. Chem. Soc., 27, 2392, 1962), by William R. Miller et al. (Ind. Eng. Chem. Prod. Res. Develop., Vol 10, No. 4, 1971) and by R. B. Perkins, Jr. et al. (Journal of the American Oil Chemists' Society, Vol 52, Nov. 1975); processes for producing azelaic acid are also known and described in Ullmann's Encyclopedia of Industrial Chemistry, fifth edition, volume A 8, pages 523–539, and in the Kirk-Othmer Enc., Vol. 7, page 623. These known processes are all based on a complex process for the ozonolysis of fatty acids of natural origin such as oleic acid or soya oil. The ozonolysis step is delicate and intrinsically dangerous and produces, at the end of the process, a mixture of unsaturated products that are very difficult to purify and for which purification is in any case industrially possible only up to 80–90%. Furthermore, the availability and characteristics of the initial starting products fluctuate. Finally, it is unavoidable to also obtain additional co-products. For example, starting from oleic acid one obtains azelaic acid but also, unavoidably, pelargonic acid, with severe limitations to the free use of the individual products.

A process for synthesizing 9 amino nonanoic acid, starting from sabacic acid by means of a monoesterification, ammonolysis and Hofmann degradation has been described (W. Baoren et al, Polymer Communications, (1), 27–32, 1984). However this process has a very low selectivity and after 10 years no industrial application is known.

U.S. Pat. No. 4,322,547 describes a process which is based on the catalytic iron-copper system to obtain 9 amino nonanoic acid and azelaic acid starting from cyclohexanone and acrylonitrile. This process entails the use of amounts of catalyst, by weight, that are extremely high and indeed comparable with the weight of the product obtained. Furthermore, the copper must be introduced in the process before the iron, and therefore after mixing it is very difficult to separate the iron from the copper to recycle them; problems accordingly arise in disposing of the used and mixed catalyst. The by-products that are obtained are furthermore very difficult to separate.

Due to the above indicated reasons, after 15 years this process has had no industrial application, whereas the above described ozonolysis process is still industrially in use after more than 20 years.

The aim of the present invention is therefore to solve the problems and drawbacks of known processes, allowing to obtain highly pure products that have high selectivity so as to attain the "polymer-grade" purity required to produce polyamides 9 or 6,9 and "pharmaceutical-product grade" purity for azelaic acid.

An object is to start from industrial products of petrochemical origin that have a low cost and are widely available.

Another object is to allow to obtain a single desired final product without accessory co-productions.

This aim, these objects and others are achieved by the process according to the invention for producing an omega-functionalized aliphatic-chain carboxylic acid with more than 7 carbon atoms, which includes the following steps:

(i) the addition, in a basic environment, of the compound with formula (1)

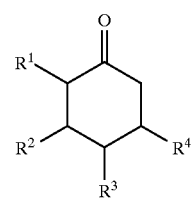
(1)

and of the compound with formula (2)

(2)

where each one of $R^1$, $R^2$, $R^3$, and $R^4$ is: hydrogen, alkyl, alkyl aryl, halogen, or hydroxyl; $R^5$ is Y or a group that can be transformed into Y with known methods: Y is —COOH, —CN, —CONH$_2$, or COOR$^6$; and $R^6$ is an optionally substituted alkyl or aryl radical, obtaining the compound with formula (3)

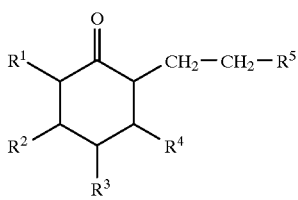

where $R^1$–$R^5$ have the above specified meaning;

(ii) the oxidation of the compound with formula (3), obtaining the compound with formula (4)

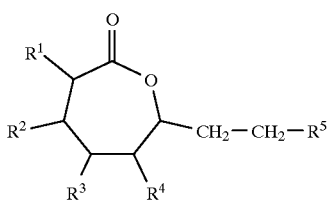

where $R^1$–$R^5$ have the above specified meaning;

(iii) the isomerization, hydrogenation, hydrogenolysis or hydrolysis of the compound with formula (4), obtaining an omega-functionalized aliphatic-chain carboxylic acid.

A first embodiment of the process is illustrated by way of non-limitative example in the following reaction diagram (I):

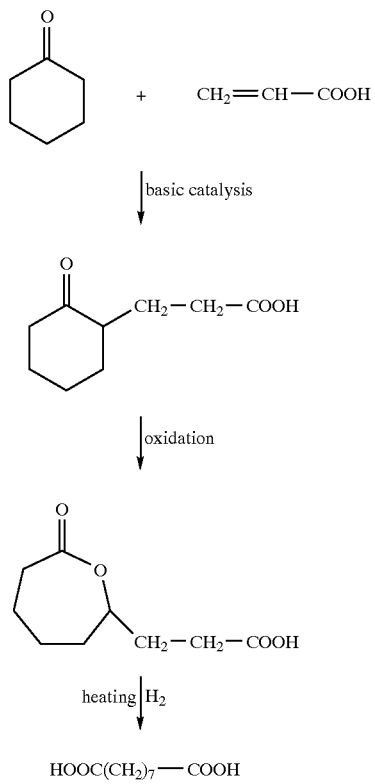

Other embodiments of the process are shown by way of non-limitative example in the following reaction diagram (II):

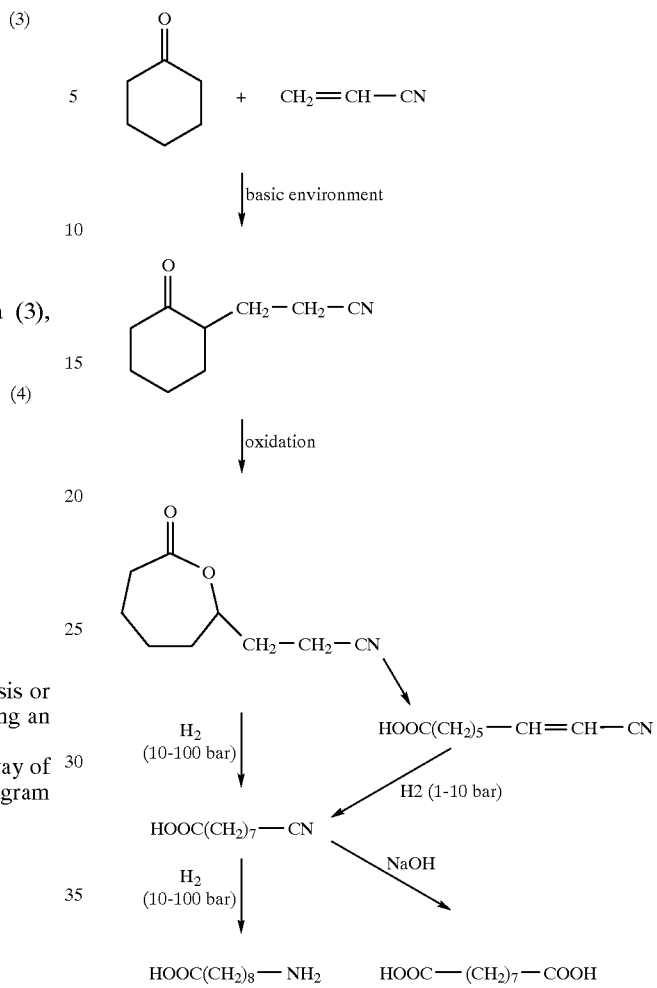

Preferably, step (i) is performed in a basic environment, more preferably in the presence of a compound chosen among ammonia and primary, secondary or tertiary aliphatic and alicyclic amines. The temperature of the reaction in step (i) is preferably between 20 and 160° C., more preferably between 40 and 140° C., and more preferably between 60 and 100° C.

The compound with formula (3) can be constituted for example by: 3-(2-cyclohexanoyl)propionitrile, 3-(2-cyclohexanoyl) propionic acid, methyl 3-(2-cyclohexanoyl) propionate, butyl 3-(2-cyclohexanoyl)propanate.

Step (ii) can be performed in the presence of an oxidizing agent chosen among hydrogen peroxide, an organic peracid and molecular oxygen. Preferably, the organic peracid is an aliphatic, alicyclic or aromatic peracid, more preferably constituted by cyclohexane percarboxylic acid, optionally substituted in its cycloaliphatic ring. This peracid has the specific advantage that it can be obtained starting from hexahydrobenzoic acid, which is a widely available, highly pure and low-cost product.

The compound with formula (4) can be recovered by extraction from the reaction mixture; in this case the organic acid remains in solution and is reoxidized into peracid and recycled.

Preferably, step (ii) is performed in the presence of an organic acid and of hydrogen peroxide, more preferably in the presence of aliphatic, cycloaliphatic or aromatic acids and of hydrogen peroxide, even more preferably in the presence of cyclohexane carboxylic acid, possibly substituted in its cycloaliphatic acid, and of hydrogen peroxide. The water can be advantageously removed, so that the compound with formula (4) can be recovered by extraction and the organic acid and the unreacted compound with formula (3) can be recycled.

As an alternative, according to another embodiment, step (ii) is performed with molecular oxygen in the presence of a catalyst, for example a Ni catalyst complexed with 1,3-diketone or an iron oxide and an aldehyde.

Step (ii) is advantageously performed at a temperature between −25° C. and 150° C., preferably between 40° C. and 70° C.

Step (ii) can be performed in a solution of an organic solvent chosen among: aliphatic hydrocarbons with 5 to 10 carbon atoms, halogenated hydrocarbons, aromatic hydrocarbons, and aliphatic and aromatic esters. Preferably, the organic solvent is chosen between hexane and ethyl acetate.

In step (ii), the molar ratio between the compound with formula (3) and said organic peracid can be between 0.25 and 10, preferably between 0.8 and 1.2. The concentration by weight of the reagents in the solution can be comprised between 1% and 100%, preferably between 15% and 40%.

Step (iii) can be performed at a temperature between 150 and 600° C., preferably at a temperature between 250 and 570° C., more preferably at a temperature between 350 and 550° C.

According to a first embodiment, step (iii) is performed in the presence of a hydrogenation catalyst and of hydrogen, obtaining an omega-functionalized aliphatic-chain carboxylic acid.

According to a second embodiment, step (iii) comprises an intermediate step during which one obtains a compound with formula (5)

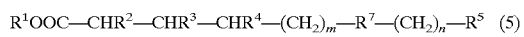

where $R^1$–$R^5$ have the above specified meaning; $R^7$ is CH=CH or CHR$^8$—CH$_2$; $R^8$ is OH, OCOCH$_3$, OCH$_3$, OEt, or halogen; m is 0, 1 or 2; n is 0 or 1; and m+n is 1 or 2. The compound with formula (5) can then be hydrogenated, obtaining an omega-functionalized aliphatic-chain carboxylic acid. Preferably, this second embodiment includes an intermediate step during which a compound with formula (6) is obtained:

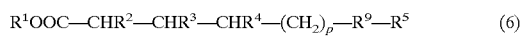

where $R^1$–$R^5$ have the above specified meaning, $R^9$ is CH$_2$—CH=CH or CH=CH—CH$_2$, and p is 0 or 1. The compound with formula (6) can then be hydrogenated, obtaining an omega-functionalized aliphatic-chain carboxylic acid.

According to a third embodiment, the intermediate step is followed by a final step wherein the compound with formula (5) or formula (6) is hydrogenated at a pressure between 1 and 10 bar (0.1 and 1 MPa), preferably between 2 and 5 bar (0.2 and 0.5 MPa), and at a temperature between 20 and 200° C., preferably between 30 and 130° C., more preferably between 40 and 70° C., obtaining a compound with the formula (7):

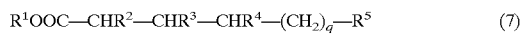

where $R^1$–$R^5$ have the above specified meaning and q is 3 or 4. If $R^5$ is CN, the compound with formula (7) can subsequently be hydrogenated at a hydrogen pressure between 1 and 200 bar, preferably between 2 and 130 bar, obtaining an omega-functionalized aliphatic-chain carboxylic acid.

According to a fourth embodiment, step (iii) includes hydrolysis performed in an aqueous solution, in the presence of an agent chosen among NaOH, alcohol and acetic acid. In this case it is possible to obtain an intermediate step in which it is possible to isolate a compound with formula (8):

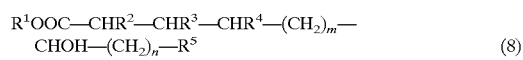

where $R^1$–$R^5$ have the above specified meaning; m is 0, 1 or 2; n is 0, 1 or 2; and m+n is 2 or 3. The compound with formula (8) can then be hydrogenated, obtaining an omega-functionalized aliphatic-chain carboxylic acid.

The invention furthermore relates to the following intermediate product, which can be isolated from the reaction environment: the compound with formula (4)

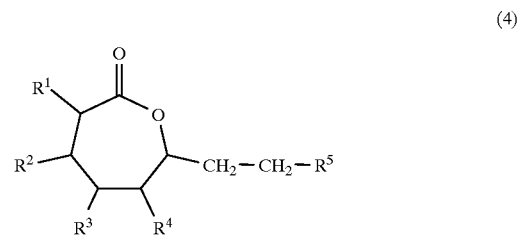

where each one of $R^1$, $R^2$, $R^3$, and $R^4$ is: hydrogen, alkyl, alkyl aryl, halogen, or hydroxyl; $R^5$ is Y or a group that can be transformed into Y with known methods: Y is —COOH, —CN, CONH$_2$, or COOR$^6$; and $R^6$ is an optionally substituted alkyl or aryl radical. According to preferred embodiments, the compound with formula (4) can have one of the following formulas:

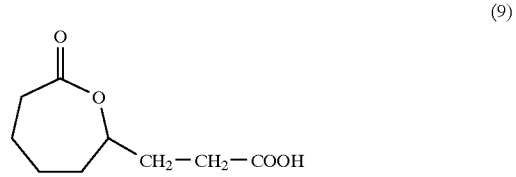

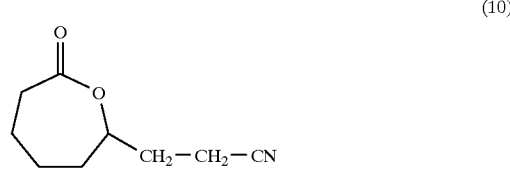

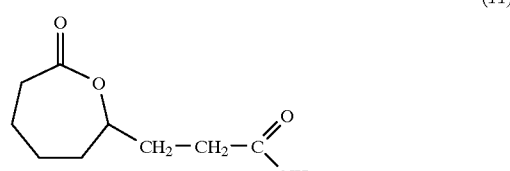

-continued

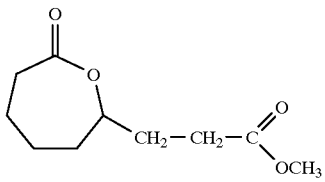
(12)

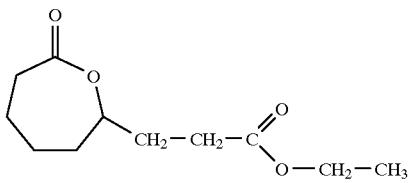
(13)

The invention furthermore relates to the following intermediate products that can be isolated from the reaction environment.

The compound with formula (5)

$$R^1OOC-CHR^2-CHR^3-CHR^4-(CH_2)_m-R^7-(CH_2)_n-R^5 \quad (5)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods; Y is —COOH, —CN, $CONH_2$ or $COOR^6$; $R^6$ is an optionally substituted alkyl or aryl radical; $R^7$ is CH=CH or $CHR^8-CH_2$; $R^8$ is OH, $OCOCH_3$, $OCH_3$, OEt, or halogen; m is 0, 1 or 2; n is 0 or 1; and m+n is 1 or 2.

The compound with formula (6)

$$R^1OOC-CHR^2-CHR^3-CHR^4-(CH_2)_p-R^9-R^5 \quad (6)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods; Y is —COOH, —CN, $CONH_2$ or $COOR^6$; $R^6$ is an optionally substituted alkyl or aryl radical; $R^9$ is $CH_2$—CH=CH or CH=CH—$CH_2$, and p is 0 or 1.

The compound with formula (7)

$$R^1OOC-CHR^2-CHR^3-CHR^4-(CH_2)_q-R^5 \quad (7)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods; Y is —COOH, —CN, $CONH_2$ or $COOR^6$; $R^6$ is an optionally substituted alkyl or aryl radical; and q is 3 or 4.

The compound with formula (8)

$$R^1OOC-CHR^2-CHR^3-CHR^4-(CH_2)_m-CHOH-(CH_2)_n-R^5 \quad (8)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods; Y is —COOH, —CN, $CONH_2$ or $COOR^6$; $R^6$ is an optionally substituted alkyl or aryl radical; m is 0, 1 or 2; n is 0, 1 or 2; and m+n is 2 or 3.

The compound with formula (15)

$$R^1OOC-CHR^2-CHR^3-CHR^4-(CH_2)_z-CN \quad (15)$$

where each one of $R^1$, $R^2$, $R^3$, and $R^4$ is: hydrogen, alkyl, alkyl aryl, halogen, or hydroxyl; and z is 3 or 4.

The following compounds with formulas (14) and (16) are preferred embodiments:

$$HOOC-(CH_2)_5-CH=CH-CN \quad (14)$$

$$HOOC-(CH_2)_7-CN \quad (16)$$

The following examples are enclosed by way of non-limitative example of the present invention.

EXAMPLE 1

7-cyanoethyl-2-oxepanone

A reactor is loaded with 500 g of 3-(2-cyclohexanolyl) propionitrile in 1000 ml of n-hexane; the reaction mixture is heated to 50° C. and a solution of 520 g of perhexahydrobenzoic acid in 3000 ml of n-hexane is added. The reaction mixture is kept agitated for three hours at 55° C. and then the lower phase, mainly formed by 7-cyano-ethyl-2-oxepanone and hexahydrobenzoic acid, is separated, while the upper phase contains hexahydrobenzoic acid and small amounts of unreacted cyanoketone. Treatment of the lower phase with n-hexane allows to isolate 515 g of 7-cyanoethyl-2-oxepanone, equal to a yield of over 93%, with 99% ketone conversion. The 7-cyanoethyl-2-oxepanone (m.p. 35° C.) is identified by means of I.R. (KBr) analytical techniques: 2970, 2870, 2245, 1720, 1175 cm$^{-1}$ and mass spectrometry by electron-impact ionization (70 eV): 168, 150, 139, 122, 113, 95, 84, 67, 55, 41. Analytically calculated values for $C_9H_{11}NO_2$ (167.21): C 64.65%, H 7.83%, N 8.38%. Found: C 64.51%, H 7.98%, N 8.46%.

EXAMPLE 1a 3-(2-cyclohexanoyl)propionitrile

A reactor is loaded with 980 g of cyclohexanone, 22 g of acrylonitrile, 18 g of glacial acetic acid, 40 g of cyclohexylamine and 11 g of hydroquinone. The reaction mixture is slowly raised to 130° C. and then kept at this temperature for 2 hours. The reaction product is cooled to 25° C., the catalyst is filtered out and distillation is performed, collecting 552 g of 3-(2-cyclohexanoly)propionitrile (b.p. 113–116° C./4 mm Hg).

EXAMPLE 2

7-cyanoethyl-2-oxepanone

A reactor is loaded with 151 g of 3-(2-cyclohexanoyl) propionitrile in 500 ml of n-hexane and 260 g of m-chloroperbenzoic acid (70% titer) dissolved at 50° C. in 2000 ml of n-hexane in 30 minutes. The solution is heated to 55° C. for 15 hours. Cooling of the solution separates, in crystalline form, part of the m-chlorobenzoic acid which is scarcely soluble in the system, together with a heavy liquid phase which is formed by 7-cyanoethyl-2-oxepanone and by m-chlorobenzoic acid. 71.5 g of 7-cyanoethyl-2-oxepanone, impure with m-chlorobenzoic acid, are recovered from the lower phase. 24 g of 7-cyanoethyl-2-oxepanone are recovered from the upper phase by concentration and several crystallizations. Conversion over the initial ketone is 85%. Yield on the converted amount is 57%.

EXAMPLE 3

7-cyanoethyl-2-oxepanone

A reactor is loaded with 151 g of 3-(2-cyclohexanoyl) propionitrile in 500 ml of glacial acetic acid. This solution receives the addition of 210 g of 40% peracetic acid in 2 hours, keeping the temperature between 30 and 40° C. After the addition has been completed, the reaction mixture is heated to 60° C. for 3 hours to complete the reaction. The

9 reaction mixture is distilled in vacuum, recovering acetic acid and obtaining 150 g of an oily residue that contains 35% 7-cyanoethyl-2-oxepanone together with 65% by-products, with 98% conversion of the initial ketone (GLC analysis).

EXAMPLE 4

8-cyano-7-octenoic acid 167 g of 7-cyanoethyl-2-oxepanone are heated in a reactor to a temperature of 450° C. in inert atmosphere, collecting 0.5 g/minute of liquid condensed product mainly formed by 8-cyano-7-octenoic acid, with 95% lactone conversion and 93% selectivity.

The product, with a b.p. of 155° C. at 0.05 torr, was identified with I.R. (film) analysis techniques: 3500, 3050, 3000, 2940, 2870, 2260, 1710, 1610, 1420, 975 cm$^{-1}$ and mass spectrometry by electron-impact ionization (70 eV): 168, 149, 121, 94, 80, 67, 55, 53, 41, 39. Analytically calculated values for $C_9H_{13}NO_2$ (167.21): C 64.65%, H 7.83%, N 8.30%. Found: C 64.55%, H 8.01%, N 8.45%.

EXAMPLE 5

8-cyanooctanoic acid 167 g of 8-cyano-7-octenoic acid dissolved in 800 ml of toluene are hydrogenated selectively at 2 bar in an autoclave in the presence of 10 g of Pd on charcoal at 5% at 50° C. for 5 hours. After filtration of the catalyst and evaporation of the solvent, 165 g of an oil that distills at 150° C. at 0.05 torr are recovered. The product has been identified as 8-cyanooctanoic acid by I.R. (film) analysis techniques: 3400, 3000, 2950, 2875, 2260, 1710, 1430 cm$^{-1}$ and mass spectrometry by electron-impact ionization (70 eV): 170, 152, 140, 123, 110, 94, 83, 69, 55, 41. Analytically calculated values for $C_9H_{15}NO_2$ (169.22): C 63.88%, H 8.93%, N 8.28%. Found: C 63.76%, H 9.12%, N 8.37%.

EXAMPLE 5a 8-cyanooctanoic acid

In a reactor with a catalyst composed of palladium on carbon at 5% deposited on the walls, 167 g of 7-cyanoethyl-2-oxepanone are heated to 500° C. in a hydrogen atmosphere, collecting 1 g/minute of liquid condensed product mainly formed by 8-cyanooctanoic acid with 95% lactone conversion and 80% selectivity.

EXAMPLE 6 azelaic acid 83.5 g of 8-cyanooctanoic acid dissolved in 300 ml of dimethyl ether ethylene glycol are heated to 130° C. for 4 hours in the presence of 50g of 40% caustic soda. After cooling, the reaction mixture is diluted with water, then acidified to pH 5 with diluted sulfuric acid, and then the precipitated solid is filtered. After drying, 92 g of azelaic acid with a m.p. of 107° C. are obtained.

EXAMPLE 6a azelaic acid 84.5 g of 8-cyanooctanoic acid are heated to 130° C. for 10 hours in the presence of 250 ml of concentrated sulfuric acid. After cooling, the reaction mixture is diluted with water and ice and the solid crystalline precipitate is filtered. After drying, one obtains 90 g of azelaic acid with a m.p. of 107° C.

EXAMPLE 7

9-aminononanoic acid 167 g of 8-cyano-7-octanoic acid dissolved in 1000 ml of propyl alcohol are hydrogenated at 50° C. and 80 bar for 10 hours, using 20 g of Ni-Raney as a catalyst. The catalyst is filtered out and the solution is concentrated. Cooling and purification produce 9-aminononanoic acid in the form of a crystalline solid product with a m.p. of 190–193° C.

EXAMPLE 8

9-aminononanoic acid 84.5 g of 8-cyanooctanoic acid dissolved in 500 ml of isopropyl alcohol saturated with $NH_3$ are hydrogenated at 50° C. and 80 bar for 3 hours, using 20 g of cobalt-Raney as catalyst. The catalyst is filtered out and the solution is concentrated. Cooling and purification produce 9-aminononanoic acid (80 g) in the form of a crystalline solid product with a m.p. of 190–192° C.

We claim:

1. Process for producing an omega-functionalized aliphatic-chain carboxylic acid with more than 7 carbon atoms, comprising the following steps:

(i) the addition of the compound with formula (1)

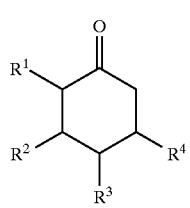

(1)

and of the compound with formula (2)

(2)

where each one of $R^1$, $R^2$, $R^3$, and $R^4$ is: hydrogen, alkyl, alkyl aryl, halogen, or hydroxyl; $R^5$ is Y or a group that can be transformed into Y with known methods: Y is —COOH, —CN, —CONH$_2$, or COOR$^6$; and $R^6$ is an alkyl or aryl radical, obtaining the compound with formula (3)

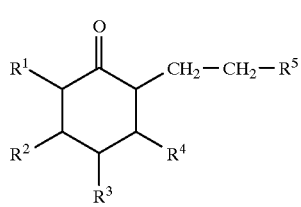

(3)

where $R^1$–$R^5$ have the above specified meaning;

(ii) the oxidation of the compound with formula (3), obtaining the compound with formula (4)

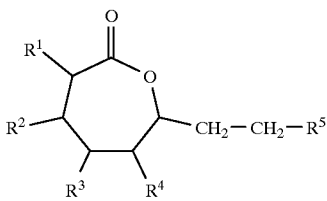

where $R^1$–$R^5$ have the above specified meaning;

(iii) the isomerization, hydrogenation, hydrogenolysis or hydrolysis of the compound with formula (4), obtaining an omega-functionalized aliphatic-chain carboxylic acid.

2. Process according to claim 1, wherein said step (i) is performed in the presence of a compound chosen from the group consisting of ammonia, and primary, secondary, tertiary aliphatic and alicyclic amines.

3. Process according to claim 1, wherein said step (i) is performed at a temperature between 20 and 160° C.

4. Process according to claim 3 wherein said step (i) is performed at a temperature between 80–150° C.

5. Process according to claim 1, wherein said step (ii) is performed in the presence of an oxidizing agent.

6. Process according to claim 5, wherein in said step (ii) the oxidizing agent is an organic alicyclic, aliphatic or aromatic percarboxylic acid.

7. Process according to claim 6, wherein in said step (ii) the oxidizing agent is cyclohexane percarboxylic acid.

8. Process according to claim 1, wherein the compound of formula (4) is recovered by extraction from the reaction mixture and the organic acid remains in solution and is reoxidized into peracid and recycled.

9. Process according to claim 1, wherein said step (ii) is performed in the presence of an organic acid and hydrogen peroxide.

10. Process according to claim 1, wherein said step (ii) is performed in the presence of an aliphatic, cycloaliphatic or aromatic carboxylic acid and hydrogen peroxide.

11. Process according to claim 10, wherein said step (ii) is performed in the presence of cyclohexane carboxylic acid and hydrogen peroxide.

12. Process according to claim 11, wherein the water is removed, the compound with formula (4) is recovered by extraction, and the organic acid and the unreacted compound with formula (3) are recycled.

13. Process according to claim 1, wherein said step (ii) is performed is performed at a temperature between –25° C. and 150° C.

14. Process according to claim 1 wherein said step (iii) comprises an intermediate step during which a compound with formula (5) is obtained:

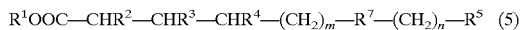

where $R^1$–$R^5$ have the above specified meaning; $R^7$ is CH=CH or $CHR^8$—$CH_2$; $R^8$ is OH, $OCOCH_3$, $OCH_3$, OEt, or halogen; m is 0, 1 or 2; n is 0 or 1; and m+n is 1 or 2, said compound with formula (5) being subsequently hydrogenated, obtaining an omega-functionalized aliphatic-chain carboxylic acid.

15. Process according to claim 1, wherein said step (iii) comprises an intermediate step during which a compound with formula (6) is obtained:

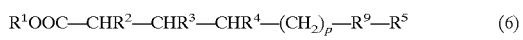

where $R^1$–$R^5$ have the above specified meaning, R9 is $CH_2$—CH=CH or CH=CH—$CH_2$, and p is 0 or 1; said compound with formula (6) being then hydrogenated, obtaining an omega-functionalized aliphatic-chain carboxylic acid.

16. Process according to claim 1, wherein said step (iii) comprises hydrolysis performed in an aqueous solution, in the presence of an agent chosen among NaOH, alcohol and acetic acid.

17. Process according to claim 16, wherein said step (iii) comprises an intermediate step in which a compound with formula (8) is obtained:

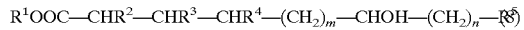

where $R^1$–$R^5$ have the above specified meaning; m is 0, 1 or 2; n is 0, 1 or 2; and m+n is 2 or 3, said compound with formula (8) being then hydrogenated, obtaining an omega-functionalized aliphatic-chain carboxylic acid.

18. Process according to claim 13 wherein, said step (ii) is performed at a temperature between 40° C. and 70° C.

19. Process according to claim 1 wherein said step (ii) is performed in a solution of an organic solvent chosen from the group consisting of aliphatic hydrocarbons with 5 to 10 carbon atoms, halogenated hydrocarbons, aromatic hydrocarbons and aliphatic and aromatic esters.

20. Process according to claim 19 wherein said step (ii) is performed in a solution of n-hexane or ethyl acetate.

21. Process according to claim 6, wherein in said step (ii) the molar ratio between said compound of formula (3) and said organic peracid is between 0.25 and 10.

22. Process according to claim 21, wherein in said step (ii) the molar ratio between said compound of formula (3) and said organic peracid is between 0.8 and 1.2.

23. Process according to claim 1, wherein in said step (ii) the concentration by weight of the reagents in the solution is between 1% and 100%.

24. Process according to claim 1, wherein in said step (ii) the concentration by weight of the reagents in the solution is between 15% and 40%.

25. Process according to claim 1, wherein said step (iii) is performed at a temperature between 150 and 600° C.

26. Process according to claim 1, wherein said step (iii) is performed at a temperature between 350 and 550° C.

27. Process according to claim 1, wherein said step (iii) is performed in the presence of a hydrogenation catalyst and of hydrogen, obtaining an omega-functionalized aliphatic-chain carboxylic acid.

28. Process according to claim 14, wherein said intermediate step is followed by a final step wherein said compound with formula (5) or formula (6) is hydrogenated at a pressure between 1 and 10 bar (0.1 and 1 MPa), obtaining a compound with formula (7):

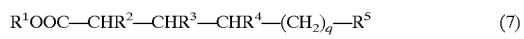

where $R^1$–$R^5$ have the above specified meaning and q is 3 or 4.

29. Process according to claim 14, wherein said intermediate step is followed by a final step wherein said compound with formula (5) or formula (6) is hydrogenated at a pressure between 2 and 5 bar (0.2 and 0.5 Mpa), obtaining a compound with formula (7), where $R^1$–$R^5$ have the above specified meaning and q is 3 or 4.

30. Process according to claim 14 wherein said intermediate step is followed by a final step wherein said compound with formulat (5) or formula (6) is hydrogenated at a temperature between 20 and 200° C., obtaining a compound

13 with formula (7), where $R^1$–$R^5$ have the above specified meaning and q is 3 or 4.

31. Process according to claim 14, wherein said intermediate step is followed by a final step wherein said compound with formula (5) or formula (6) is hydrogenated at a temperature between 40 and 70° C., obtaining a compound with formula (7), where $R^1$–$R^5$ have the above specified meaning and q is 3 or 4.

32. Process according to claim 15, wherein said intermediate step is followed by a final step wherein said compound with formula (5) or formula (6) is hydrogenated at a pressure between 1 and 10 bar (0.1 and 1 MPa), obtaining a compound with formula (7):

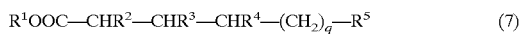

$$R^1OOC—CHR^2—CHR^3—CHR^4—(CH_2)_q—R^5 \qquad (7)$$

where $R^1$–$R^5$ have the above specified meaning and q is 3 or 4.

33. Process according to claim 15, wherein said intermediate step is followed by a final step wherein said compound with formula (5) or formula (6) is hydrogenated at a pressure between 2 and 5 bar (0.2 and 0.5 Mpa), obtaining a compound with formula (7), where $R^1$–$R^5$ have the above specified meaning and q is 3 or 4.

34. Process according to claim 15, wherein said intermediate step is followed by a final step wherein said compound with formula (5) or formula (6) is hydrogenated at a temperature between 20 and 200° C., obtaining a compound with formula (7), where $R^1$–$R^5$ have the above specified meaning and q is 3 or 4.

35. Process according to claim 15, wherein said intermediate step is followed by a final step wherein said compound with formula (5) or formula (6) is hydrogenated at a temperature between 40 and 70° C., obtaining a compound with formula (7), where $R^1$–$R^5$ have the above specified meaning and q is 3 or 4.

36. Process according to claim 35, wherein $R^5$ is CN, said compound with formula (7) being subsequently hydrogenated at a hydrogen pressure between 1 and 200 bar, obtaining an omega-functionalized aliphatic-chain carboxylic acid.

37. Process according to claim 35, wherein $R^5$ is CN, said compound with formula (7) being subsequently hydrogenated at a hydrogen pressure between 2 and 130 bar, obtaining an omega-functionalized aliphatic-chain carboxylic acid.

38. Process according to claim 1, wherein said step (iii) comprises hydrolysis performed in an aqueous solution, in the presence of an agent chosen amount NaOH, alcohol and acetic acid.

39. Process according to claim 38, wherein said step (iii) comprises an intermediate step in which a compound with formula (8) is obtained:

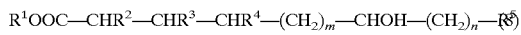

$$R^1OOC—CHR^2—CHR^3—CHR^4—(CH_2)_m—CHOH—(CH_2)_n—R^5$$

where $R^1$–$R^5$ have the above specified meaning, m is 0, 1 or 2; and m+n is 2 or 3, said compound with formula (8) being then hydrogenated, obtaining an omega-functionalized aliphatic-chain carboxylic acid.

14

40. Compound with formula (4)

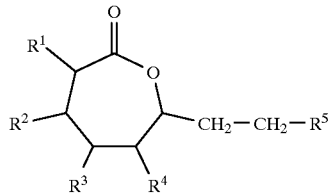

(4)

where each one of $R^1$, $R^2$, $R^3$, and $R^4$ is: hydrogen, alkyl, alkyl aryl, halogen, or hydroxyl; $R^5$ is Y or a group that can be transformed into Y with known methods: Y is —COOH, —CONH$_2$, or COOR$^6$; and $R^6$ is an optionally substituted alkyl or aryl radical.

41. Compound according to claim 40, with formula (9)

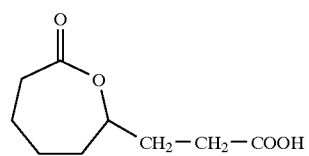

(9)

42. Compound according to claim 40, with formula (11)

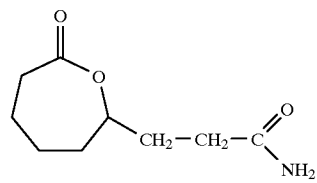

(11)

43. Compound according to claim 40, with formula (12)

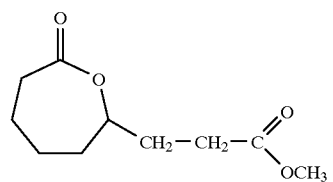

(12)

44. Compound according to claim 40, with formula (13)

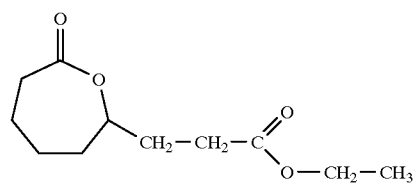

(13)

45. Compound with formula (5)

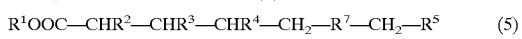

$$R^1OOC—CHR^2—CHR^3—CHR^4—CH_2—R^7—CH_2—R^5 \qquad (5)$$

where each one of $R^1$, $R^2$, $R^3$, and $R^4$ is: hydrogen, alkyl, alkyl aryl, halogen, or hydroxyl; $R^5$ is Y or a group that can be transformed into Y with known methods; Y is —COOH, —CN, CONH$_2$ or COOR$^6$; R$^6$ is an optionally substituted alkyl or aryl radical; R$^7$ is CH=CH or CHR$^8$—CH$_2$; R$^8$ is OH, OCOCH$_3$, OCH$_3$, OEt, or halogen.

46. Compound with formula (8)

$$R^1OOC—CHR^2—CHR^3—CHR^4—(CH_2)_m CHOH—(CH_2)_n—R^5 \quad (8)$$

where each one of R$^1$, R$^2$, R$^3$, and R$^4$ is: hydrogen, alkyl, alkyl aryl, halogen, or hydroxyl; R$^5$ is Y or a group that can be transformed into Y with known methods; Y is —COOH, —CN, CONH$_2$ or COOR$^6$; R$^6$ is an optionally substituted alkyl or aryl radical; m is 0, 1 or 2; n is 0, 1 or 2; and m+n is 2 or 3.

47. Compound according to formula (14)

$$HOOC—(CH_2)_5—CH=CH—CN \quad (14).$$

48. Compound with formula (15)

$$R^1OOC—CHR^2—CHR^3—CHR^4—(CH_2)_z—CN \quad (15)$$

where each one of R$^1$, R$^2$, R$^3$, and R$^4$ is: alkyl, alkyl aryl, halogen, or hydroxyl; and z is 3 or 4.

* * * * *